United States Patent
Lin et al.

(10) Patent No.: US 7,015,248 B2
(45) Date of Patent: Mar. 21, 2006

(54) USE OF ABIETIC ACID AND DERIVATIVES THEREOF FOR INHIBITING CANCER

(75) Inventors: Chi-Hung Lin, Taoyuan (TW); Hsin-Shiu Chuang, Taoyuan (TW)

(73) Assignee: Xiamen Ever-Health Bio-Tech. Co. Ltd, Xiamen (CN)

( * ) Notice: Subject to any disclaimer, the term of this patent is extended or adjusted under 35 U.S.C. 154(b) by 0 days.

(21) Appl. No.: 10/672,683

(22) Filed: Sep. 26, 2003

(65) Prior Publication Data

US 2004/0063788 A1 Apr. 1, 2004

Related U.S. Application Data

(60) Provisional application No. 60/414,153, filed on Sep. 26, 2002.

(51) Int. Cl.
*A61K 31/40* (2006.01)
(52) U.S. Cl. .................................................. 514/557
(58) Field of Classification Search ................ 514/557
See application file for complete search history.

(56) References Cited

U.S. PATENT DOCUMENTS 5,248,696 A * 9/1993 Bang et al. ................. 514/557
2003/0092674 A1 * 5/2003 Saxena et al. ................ 514/63

OTHER PUBLICATIONS

Cecil Textbook of Medicine, Godman et al. eds., 21st Ed. vol. 1 (2000), pp 1060-1074.*

Aranda et al., 1997, *Bichimica et Biophysica Acta*, 1327: 171-180 "The interaction of abietic acid with phospholipid membranes."

Lee et al., 1997, *Journal of Chromatography A*, 763:221-226 "High-performance liquid chromatographic determination of dehydroabietic and abietic acids in traditional Chinese medications."

Luong et al., 1999, *Electrophoresis*, 20:1546-1554 "Separation of resin acids using cyclodextrin-modified capillary electrophoresis."

Mellanen et al., 1996, *Toxicology and Applied Pharmacology*, 136:381-388 Wood-Derived Estrogens: Studies in Vitro with Breast Cancer Cell Lines and in Vivo in Trout.

Ohtsu et al., 2001, *Planta Med*, 67:55-60 "Abietane Diterpenoids from the Cones of *Larix kaempferi* and their Inhibitory Effects on Epstein-Barr Virus Activation."

Vobel et al., 1996, *The Journal of Biological Chemistry*, 271(38):23262-23268 "Abietadiene Synthase from Gand Fir (*Abies grandis*)."

Ulusu et al., 2002, *Phytotherapy Research*, 16:88-90 "Abietic Acid Inhibits Lipoxygenase Activity."

Villalain, 1996, *Eur. J. Biochem.*, 241:586-593 "Location of cholesterol in model membranes by magic-angle-sample-spinning NMR."

Villalain, 1997, *Biochimica et Biophysica Acta*, 1328:281-289 Location of the toxic molecule abietic acid in model membranes by MAS-NMR.

* cited by examiner

*Primary Examiner*—Raymond J. Henley, III
(74) *Attorney, Agent, or Firm*—Merchant & Gould P.C.

(57) ABSTRACT

The present invention relates to a novel use of abietic acid or derivatives thereof for inhibiting the growth of a cancer cell or treating a cancer, preferably, reducing the tumor size of the cancer.

9 Claims, 4 Drawing Sheets

USE OF ABIETIC ACID AND DERIVATIVES THEREOF FOR INHIBITING CANCER

This application claims the benefit of Provisional Application No. 60/414,153, filed Sep. 26, 2002, which is incorporated by reference herein in its entirety.

FIELD OF THE INVENTION

The present invention relates to a new use of abietic acid or derivatives thereof for inhibiting the growth of a cancer cell, treating a cancer, modulating the permeability of a plasma membrane of a cell, or improving the therapeutic effect of an anti-cancer agent.

BACKGROUND OF THE INVENTION

Abietic acid, a major ingredient in pine resin, is a naturally toxic compound with potential hazard to animals and plants (Gardner D R et al., 1999, *Journal of Natural Toxins.* 8(1): 27–34). Exposure to such compound may cause various skin and mucosal symptoms, such as allergic dermatoses and contact urticaria (el Sayed F et al., 1995, *Contact Dermatitis.* 32(6): 361–2; and Estlander et al., 2001, *Contact Dermatitis.* 44(4): 213–7). Some traditional Chinese medicaments contain the ingredients of dehydroabietic acid and abietic acid, and a number of patients with dermatitis are sensitive to such ingredients (Lee et al., 1997, *Journal of Chromatography. A.* 763(1–2): 221–6). In addition, occupational exposure to cedar, pinewoods and pine resin (colophony) may cause asthma and chronic lung disease. Some studies suggested that plicatic and abietic acids were the ingredients responsible for inducing asthmatic reactions that occur in cedar-wood and colophony workers (Ayars et al., 1989, *Journal of Allergy & Clinical Immunology.* 83(3): 610–8). Recently, it is also found that abietic acid may cause a dose and time-dependent destruction of alveolar, tracheal, and bronchial epithelial cells, and may induce sloughing of bronchial epithelial in vivo. However, the mechanisms for the observed cellular toxic effects are currently unknown.

Furthermore, other biological activities of abietic acid have been reported. For instance, abietic acid or derivatives thereof could exhibit inhibitory effects on the activation of Epstein-Barr virus early antigens (Ohtsu et al., 2001, *Planta Medica.* 67(1): 55–60), the aggregation of platelet (Cheung et al., 1994, *Arzneimittel-Forschung.* 44(1): 17–25) and thrombosis (Liu et al., 1985, *Journal of Traditional Chinese Medicine.* 5(2): 115–8). They could also modulate the functions of synapsomal structure of neuronal cells (Nicholson, 1994, *Biochemical Society Transactions.* 22(2): 226S).

Recently, many intensive studies focus on the antibacterial activity of abietic acid, especially on the interaction of abietic acid with zinc oxide, rosin and other resin acids and their combination (Soderberg et al., 1990, *Scandinavian Journal of Plastic & Reconstructive Surgery & Hand Surgery. Supplementum.* 22: 1–87; and Soderberg et al., 1991, *Scandinavian Journal of Plastic & Reconstructive Surgery & Hand Surgery.* 25(1): 19–24). The so-called "antibacterial effects" of abietic acid might be partially caused by the anti-inflammatory activity of abietic acid. Some studies reported that abietic acid could inhibit lipoxygenase pathway at an $IC_{50}$ of 29.5±1.29 $\mu M$ and thus decrease the biosynthesis of leukotrienes in vivo and in vitro (Ulusu et al., 2002, *Phytotherapy Research.* 16(1): 88–90). In addition, abietic acid could inhibit the production of the inflammatory mediator, prostaglandin E2, in lipopolysaccharide-treated macrophages (Fernandez et al., 2001, *Journal of Pharmacy & Pharmacology.* 53(6): 867–72).

On the other hand, wood-derived compounds such as β-sitosterol have been shown to have estrogenic effects in fish. In fact, a structure analysis revealed that the chemical structure of abietic acid was similar to that of estrogenic, androgenic and steroid hormones, and a treatment with abietic acid could be estrogenic in breast cancer cells such as MCF-7 or T-47D (Mellanen et al., 1996, *Toxicology & Applied Pharmacology.* 136(2): 381–8).

Abietic acid, an amphipathic molecule, can be purified to a purity of more than 90% (Luong et al., 1999, *Electrophoresis.* 20(7): 1546–54). Recently, a number of high resolution nuclear magnetic resonance (NMR) studies have been used to analyze the location of abietic acid in cells and the interaction of abietic acid with the components of a plasma membrane to find out the mechanism of the wide actions of abietic acid. The studies indicated that abietic acid was located in the upper part of the palisade structure of a plasma membrane wherein the carboxyl group of abietic acid was in close proximity to the phospholipid ester group of the membrane but did not extend beyond the C4/C7 carbons of the phospholipid molecule of the membrane (Villalain, 1996, *Eur. J Biochem.* 241: 586–593; Villalain, 1997, *Biochimica et Biophysica Acta.* 1328(2): 281–9, 1997; Aranda and Villalain, 1997, *Biochimica et Biophysica Acta.* 1327(2):171–80). However, most of the studies were conducted on synthetic membranes and little experimental evidence linking the molecular features of abietic acid to the biological effects observed in living cells or tissues was provided. In addition, no references have reported the use of abietic acid for affecting the growth of cancer cells or treating cancers.

SUMMARY OF THE INVENTION

In one aspect, the invention provides a method for inhibiting the growth of a cancer cell comprising treating the cancer cell with an effective amount of abietic acid or derivatives thereof. The invention also provides a method for treating a cancer or preventing, alleviating or ameliorating symptoms of the cancer comprising the step of administrating an effective amount of abietic acid or derivatives thereof to a subject in need thereof.

In another aspect, the invention provides a method for modulating the permeability of a plasma membrane of a cell. The invention also provides a method for treating a disease associated with the permeability of a plasma membrane of a cell. The invention further provides a method for improving the therapeutic effect of a pharmaceutical agent.

DETAILED DESCRIPTION OF THE INVENTION

I. Definitions

Figure 1:
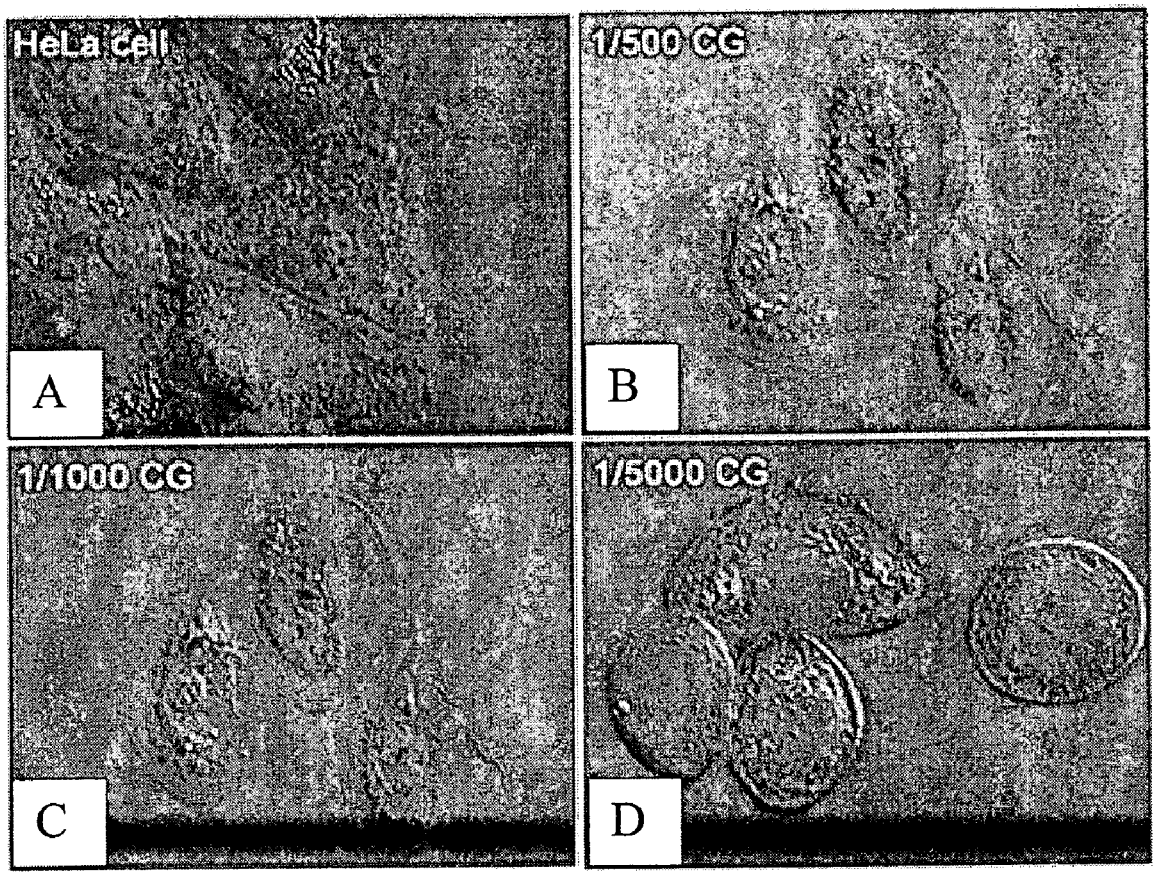
FIG. 1 shows DIC microscope images of HeLa cells without the treatment of abietic acid (panel A) or treated with 0.3 $\mu g/ml$ (1/500 dilution, panel B), 0.15 $\mu g/ml$ (1/1000 dilution, panel C) or 0.03 $\mu g/ml$ (1/5000 dilution, panel D) abietic acid, respectively.

Abietic acid is a natural irritant in pine and can be isolated from a natural pine by a conventional preparation process (Merck Index, 12th edition; Puranik P K et al., 1992, Journal of Microencapsulation. 9(4): 425–35; Luong J H et al., 1999, Electrophoresis. 20(7): 1546–54). Abietic acid is of the structure below:

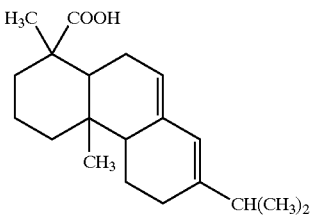

Person skilled in the art can obtain abietic acid through an artificial synthesis procedure (Vogel B S et al., 1996, Journal of Biological Chemistry. 271(38): 23262–8).

The term "derivatives" of abietic acid used herein refers to a group of compounds derived from abietic acid, which have a function substantially equivalent to that of abietic acid as described herein. For instance, the derivatives of abietic acid of the invention may be produced by incorporating a modification, such as dehydrogenation or substitution with one or more substituents, into abietic acid. According to the invention, a dehydroabietic acid and a substituted abietic acid are within the scope of the derivatives of abietic acid of the invention.

The term "an effective amount" of abietic acid or derivatives thereof used herein refers to an amount of abietic acid or the derivative thereof that is effective to inhibit the growth of cancer cells, or treat a cancer or prevent, alleviate or ameliorate symptoms of the cancer. For instance, the amount may be that of abietic acid or the derivative thereof to be administrated, effective in reducing the tumor size of the cancer to be treated according to the invention.

The term "permeability" used herein refers to the ability of a plasma membrane allowing a substance to go into or out a cell by crossing the plasma membrane.

II. Objects of the Invention

A. Uses of Abietic Acid

The invention provides a discovery of the anticancer activity of abietic acid or derivatives thereof. It has surprisingly been found that abietic acid per se can affect the growth of a variety of cancer cell lines and reduce the size of a tumor in a subject.

Accordingly, one aspect of the invention is to provide a method for inhibiting the growth of a cancer cell, which comprises the step of treating a cancer cell with an effective amount of abietic acid and derivatives thereof. In one embodiment, the method of the invention is effective in inhibiting the growth of a human cervical carcinoma cell or human heptocellular carcinoma cell.

According to the invention, abietic acid or derivatives thereof may be administrated at an amount of the abietic acid or derivatives that is effective to inhibit the growth of cancer cells. Determination of an effective amount of abietic acid or derivatives thereof used in the method of the invention is within the skill in the art. In one embodiment of the invention, abietic acid inhibits the growth of a human cervical carcinoma cell or human heptocellular carcinoma cell at a concentration of 0.01 to 0.5 µg/ml.

In addition, the method of the invention does not significantly affect the growth of a normal cell and can selectively inhibit the growth of a cancer cell. As known in the art, many conventional anti-cancer drugs have a seriously toxicity to normal cells and fail to achieve a desired selectivity in the treatment of cancers. According to the invention, abietic acid or its derivative induces a swelling phenomenon on a cancer cell at a lower concentration but induces the same phenomenon in a normal cell, which is not cancerous, at a higher concentration. In one embodiment of the invention, abietic acid is effective to induce a swelling phenomenon at a concentration of 0.03 µg/ml on a human cervical carcinoma cell, e.g., a HeLa cell line, and a human hepatocellular carcinoma cell, e.g., a HepG2 cell line, but does not affect the morphology of a normal fibroblast cell, e.g., Detroit 551, at the same concentration unless the concentration is higher than 0.15 µg/ml. Hence, the method of the invention can selectively inhibit the growth of a cancer cell without significantly producing a toxicity to a normal cell.

In another aspect, the invention provides a method for treating a cancer or preventing, alleviating or ameliorating symptoms related to the cancer, comprising the step of administrating an effective amount of abietic acid and derivatives thereof to a subject in need thereof.

In one embodiment, the method of the invention is effective in treating a breast cancer or preventing, alleviating, or ameliorating of symptoms related to the cancer in a mammal, preferably mouse or human. In another embodiment, the method of the invention can significantly reduce the tumor size of a breast cancer in a subject.

According to the invention, the abietic acid or its derivative is administrated to a subject to be treated by way of any suitable routes include, but are not limited to, oral, rectal, topical, subcutaneous, intravenous, intramuscular and nasal administration, in which an oral administration is preferred.

The effective amount of abietic acid or derivatives thereof according to the invention ranges widely and should be adjusted in accordance with various factors including the species of cancers, the route of administration and the conditions of the subject to be treated.

According to the invention, abietic acid or derivatives can be formulated with various pharmaceutically or physiologically acceptable excipients in the form of tables, hard or soft gelatin capsules, solutions, emulsions or suspensions depending on the administration route of the abietic acid or derivatives. In another embodiment of the invention, abietic acid or derivatives is administrated in combination with anti-cancer drugs or therapeutic methods known in the art, sequentially or simultaneously.

B. Composition

In still another aspect, the invention provides a composition for inhibiting the growth of a cancer cell, preferably a human cervical carcinoma cell or human heptocellular carcinoma cell. The invention provides a composition for treating a cancer or preventing, alleviating, or ameliorating symptoms related to the cancer in a subject in need thereof.

The composition of the invention comprises an effective amount of abietic acid or derivatives thereof and a pharmaceutically or physiologically acceptable excipient. Suitable excipients for the formulation of the composition of the invention include, but are not limited to, dextrin, lactose, starch, talc, tartaric acid, alcohol, glycerin, vegetable oils and waxes. The pharmaceutical composition may further contain preserving agents, solubilizing agents, stabilizing agents, wetting agents, emulsifying agents, coloring agents or buffers.

The composition of the invention can be formulated as a medicament or a dietary supplement with a suitable excipient, which may be manufactured in a manner known in the art, e.g., by means of a conventional mixing, encapsulating, dissolving, granulating, emulsifying or lyophilizing process. The composition of the invention can be formulated in the form of tables, hard or soft gelatin capsules, solutions, emulsions or suspensions depending on the administration route of the composition.

The composition of the invention can be used in combination with one or more anti-cancer drugs known in the art. When a combination use is conducted, the composition of the invention and the one or more anti-cancer drugs can be administered sequentially or simultaneously. In one embodiment, the composition of the invention may further comprise one or more anti-cancer drugs in a single dosage form. Alternatively, the composition of the invention and the anti-cancer drugs are formulated as separate dosage forms and administered simultaneously or sequentially to a subject.

III. Other Uses

It is also suggested that the mechanism of abietic acid or derivatives thereof inducing a swelling phenomenon on a cancer cell and inhibiting the growth of the cancer cell is to influence the permeability of the plasma membrane of the cancer cells.

Some substances cross the plasma membrane very easily and the membrane is very permeable to these substances, but others go across the membrane with difficulty or are even completely excluded from the membrane. In the latter case, the plasma membrane is impermeable to these substances. Normal plasma membrane permeability is important to maintain a normally physiological function of a cell. Many diseases relate to abnormal plasma membrane permeability. According to the invention, it is surprisingly found that abietic acid can modulate the permeability of a plasma membrane, such as accelerate the entrance of exogenous chemicals into a cell.

Accordingly, the invention provides a pharmaceutical composition comprising abietic acid or derivatives thereof for modulating the permeability of a plasma membrane of a cell or treating diseases associated with the permeability of a plasma membrane. In particular, the pharmaceutical composition is useful in accelerating the entrance of exogenous chemicals into a variety of cancerous cells, modulating cellular activities in responses to physiological and pathological changes of intracellular environments, such as osmotic changes, salt composition and ionic fluxes, or treating pathological conditions that involve changes of intracellular environments, such as osmotic changes, salt composition and ionic fluxes.

In another aspect, the invention provides a novel use of abietic acid or derivatives thereof for improving the therapeutic effect of a variety of known pharmaceutical agents. According to the invention, it is surprisingly found that abietic acid or derivatives thereof can be used as an adjuvant to enhance the therapeutic effects of many kinds of drugs including anticancer drugs. For instance, abietic acid can enhance the inhibitory activity of taxol against the MCF-7 breast cancer cell line, and accelerate the efficacy of mitomycin C on affecting the growth of the Hep-G2 human hepatocellular carcinoma cell line.

Accordingly, the invention provides a pharmaceutical composition comprising abietic acid or derivatives thereof for improving the therapeutic effect of a pharmaceutical agent. In one embodiment of the invention, an anticancer agent in combination with the pharmaceutical composition of the invention can produce a desired anti-tumor effect at a much lower concentration than that used without the pharmaceutical composition of the invention. In other words, the combination of an anticancer agent and the pharmaceutical composition of the invention can reduce a therapeutically effective amount of the anticancer agent and thus eliminate potential adverse effects due to a high dosage of the anticancer agent.

Many therapeutic agents are limited by their ability for entering into cells such that their therapeutic efficacies are limited. According to the invention, the efficacy of a pharmaceutical composition for improving the therapeutic effect of a therapeutic agent is caused by the activity of abietic acid or derivatives thereof for modulating the permeability of a plasma membrane of a cell, as mentioned above. Abietic acid or derivatives thereof and a therapeutic agent may be packaged in the same dosage unit or in separate dosage units. In the latter case, abietic acid or derivative thereof and a therapeutic agent may be administrated simultaneously or sequentially. The ratios of the abietic acid or derivatives thereof to the co-administrated pharmaceutical agent varies with the properties of the abietic acid or the derivatives thereof and the pharmaceutical agent, and the conditions of the subject to be treated. Persons skilled in the art would use an appropriate ratio of abietic acid or the derivatives thereof to a therapeutic agent to enhance the effect of the therapeutic agent.

In still another aspect, the invention relates to a method for modulating the permeability of a plasma membrane of a cell comprising treating the cell with abietic acid or derivatives thereof. The invention further relates to a method for treating a disease associated with the permeability of a plasma membrane of a cell comprising administrating abietic acid or derivatives thereof to a subject in need thereof. In particular, the method of the invention is effective in accelerating the entrance of exogenous chemicals into a variety of cultured cells, modulating cellular activities in responses to physiological and pathological changes of intracellular environments, such as osmotic changes, salt composition and ionic fluxes, or treating pathological conditions that involve changes of intracellular environments, such as osmotic changes, salt composition and ionic fluxes.

Furthermore, the invention provides a method for improving the therapeutic effect of a therapeutic agent comprising administrating the therapeutic agent to a subject in combination with abietic acid or derivatives thereof. Abietic acid or derivatives thereof and the pharmaceutical agent may be administrated simultaneously or sequentially. Abietic acid or derivatives thereof can enhance the therapeutic effect of a therapeutic agent by modulating the permeability of a plasma membrane, such as accelerating the entrance of exogenous chemicals into a cell. In one embodiment of the invention, a combination of abietic acid or derivatives thereof with taxol can effectively enhance the inhibitory activity of taxol against a MCF-7 breast cancer cell line. In another embodiment of the invention, the effect of mitomycin C in combination with abietic acid or derivatives thereof for controlling the growth of Hep-G2 human hepatocellular carcinoma cells is greater than that of mitomycin C along.

EXAMPLES

The present invention will become apparent with reference to the examples below. The examples described below are given by way of illustration only and are not intended to be any limitation to the present invention.

Example 1

For evaluation of the biological activities of abietic acid on mammalian cells, a time-lapsed recording using video-enhanced DIC microscopy on a variety of cultured cells, including cancerous and non-cancerous cell lines, before and after addition of abietic acid, was performed.

Abietic acid may be extracted by any conventional methods. In one embodiment of the invention, abietic acid was extracted according to the method described in Luong J H et al., 1999, *Electrophoresis*. 20(7): 1546–54, and an abietic acid stock solution at a concentration of 150 μg/ml was prepared subsequently.

HeLa cells, a human epithelioid cervical carcinoma cell line, were cultured in a standard medium under standard conditions. The HeLa cells were trypsinized and a cell suspension at a concentration of $10^5$ cells per milliliter of medium was prepared therefrom. The cell suspension was poured into a 22×22 mm coverglass and treated without abietic acid or with the abietic acid stock solution to achieve a final concentration of 0.3 μg/ml (1/500 dilution), 0.15 μg/ml (1/1000 dilution) or 0.03 μg/ml (1/5000 dilution), respectively. After a 24-hour incubation, the HeLa cells were observed with a high resolution Differential Interference Contract (DIC) microscopy. As shown in FIG. 1, the HeLa cells without treatment of abietic acid exhibited a flat and normal morphology and were well attached to the substrate (panel A). However, the HeLa cells treated with abietic acid, even at the lowest concentration of 0.03 μg/ml, exhibited a serious swelling phenomenon and became worse in a dose-dependent manner (panels B to D).

Figure 2:
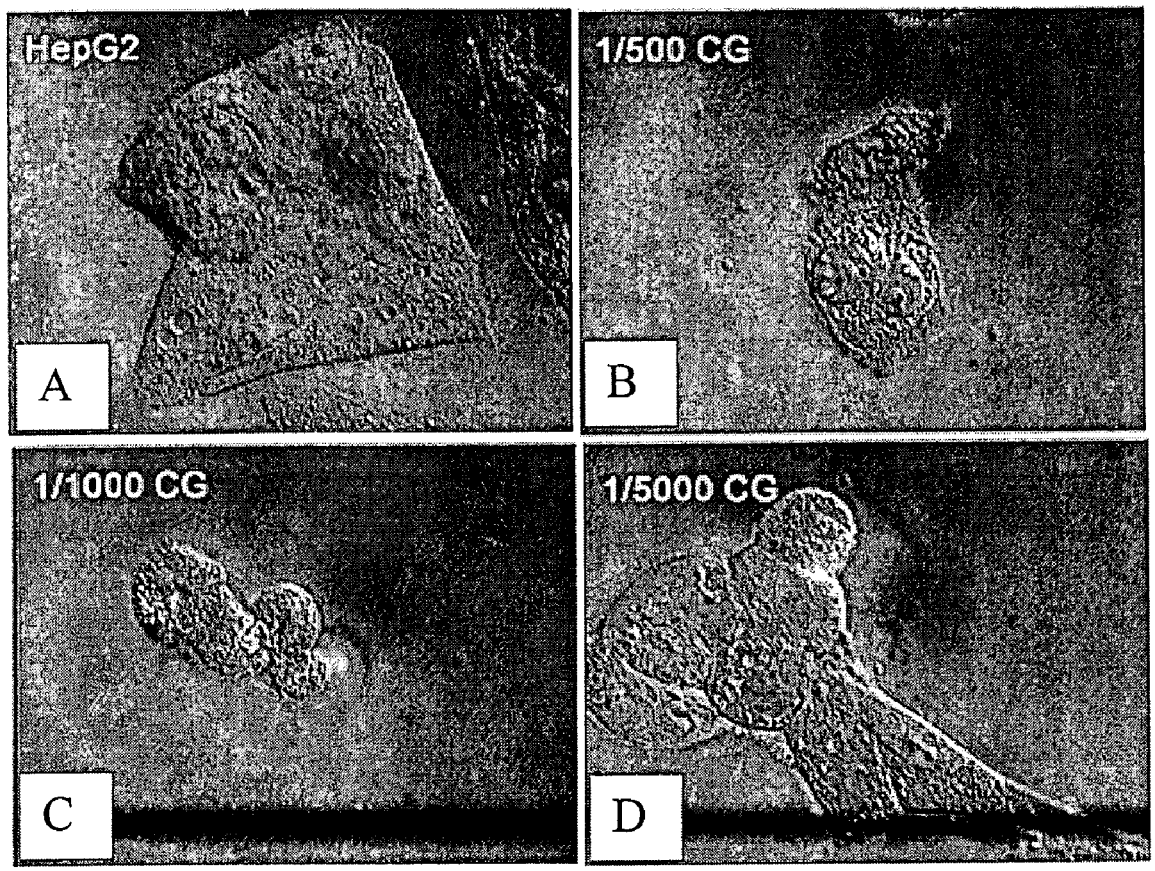
FIG. 2 shows DIC microscope images of HepG2 cells without the treatment of abietic acid (panel A) or treated with 0.3 $\mu g/ml$ (1/500 dilution, panel B), 0.15 $\mu g/ml$ (1/1000 dilution, panel C) or 0.03 $\mu g/ml$ (1/5000 dilution, panel D) abietic acid, respectively.

HepG2 cells, a human heptocellular carcinoma cell line, were cultured in a standard medium under standard conditions. The HepG2 cells were trypsinized and a cell suspension at a concentration of $10^5$ cells per milliliter of medium was prepared therefrom. The cell suspension was poured into a 22×22 mm coverglass and treated without abietic acid or with 0.3, 0.15 or 0.03 μg/ml abietic acid, respectively, as described above. After a 24-hour incubation, the HepG2 cells were observed with a high resolution DIC microscopy. As shown in FIG. 2, the HepG2 cells without treatment of abietic acid exhibited a normal and flat morphology and were well attached to the substrates (panel A). However, the HepG2 cells exhibited a different morphology when treated with 0.03 μg/ml abietic acid (panel D), and swelled when treated with 0.15 and 0.3 μg/ml abietic acid (panels C and B).

Detroit 551 normal fibroblast cells were treated without abietic acid or with abietic acid, as described above. The morphology of the normal fibroblast cells was affected when treated with 0.15 and 0.3 μg/ml abietic acid. However, the fibroblast cells treated with 0.03 μg/ml abietic acid exhibited a normal and flat morphology and were well attached to the substrates as those exhibited by the cells without the treatment of abietic acid.

It has been known that the morphology of a cell reflects the healthy condition of the cell. For instance, once a cell, which is normally attached to a substrate with a flat morphology, swells and becomes round in morphology, it means that the condition of the cell turns disadvantageous and the cell may stop the growth and be dead soon.

As shown in the example, it is now found that after exposure of abietic acid for about 24 hours at a relatively low concentration, HeLa cells and HepG2 cells, which were normally attached to a substrate where the cells grow with a flat morphology, swelled and became round in morphology. Then, the inhibition of the growth and the death of the cancer cells were observed. However, normal fibroblast cells remained flat in morphology and grew well when exposure of abietic acid for about 24 hours at the same concentration. The results demonstrate that abietic acid per se possesses a potential anti-cancer activity and a low toxicity to normal cells. Hence, abietic acid has a selective inhibition on the growth of a cancer cell without a significant toxicity to a normal cell.

Example 2

An animal experiment was conducted as follows to demonstrate the anti-cancer activity of abietic acid.

(1) Cancer Cells and Experimental Animals

Eighty Balb/c-nu/nu female nude mice, supplied by National Laboratory Animal Center in the ROC (Taiwan), four-week old, weight about 18 to 20 g, free of pinworm infection, were housed in the laboratories of the National Yang-Ming University, Taipei, ROC (Taiwan). Clear water and feeds were normally provided. The litters were replaced with new ones per three days. On the other hand, a MCF-7 breast cancer cell line was cultured under standard conditions.

(2) Pre-Treatment of Nude Mice and MCF-7 Cells

Since the nude mice were five weeks old, the nude mice were intramuscularly injected with 1.7 mg of estradiol valerate at their leg regions. On the other hand, the MCF-7 cells were treated with estradiol for 24 hours, and then trypsinized, centrifuged and recovered in the Minimum Essential Medium (MEM) medium to achieve a concentration of $2 \times 10^7$ cell/ml.

After two days following the intramuscular injection of estradiol valerate, the nude mice were subcutaneously injected with 500 μl of the estradiol-treated MCF-7 cells ($2 \times 10^7$ cell/ml) at their back regions. Once injection, the back regions swelled but became even later.

After three weeks following the injection of the MCF-7 cells, a subcutaneous tumor of 2 mm in a maximum diameter was developed at the backs of the nude mice.

(3) Treatment of Abietic Acid

These tumor containing nude mice were divided into two groups, each including 8 mice. One of the two groups were fed normally as a control group. The mice of the other group were fed with abietic acid at a dosage of 0.02667 mg per gram of the body weight of the nude mice by a gastric pipe per two days for a period of more than 12 weeks (experimental group).

(4) Measurement of Tumor Size

Figure 3:
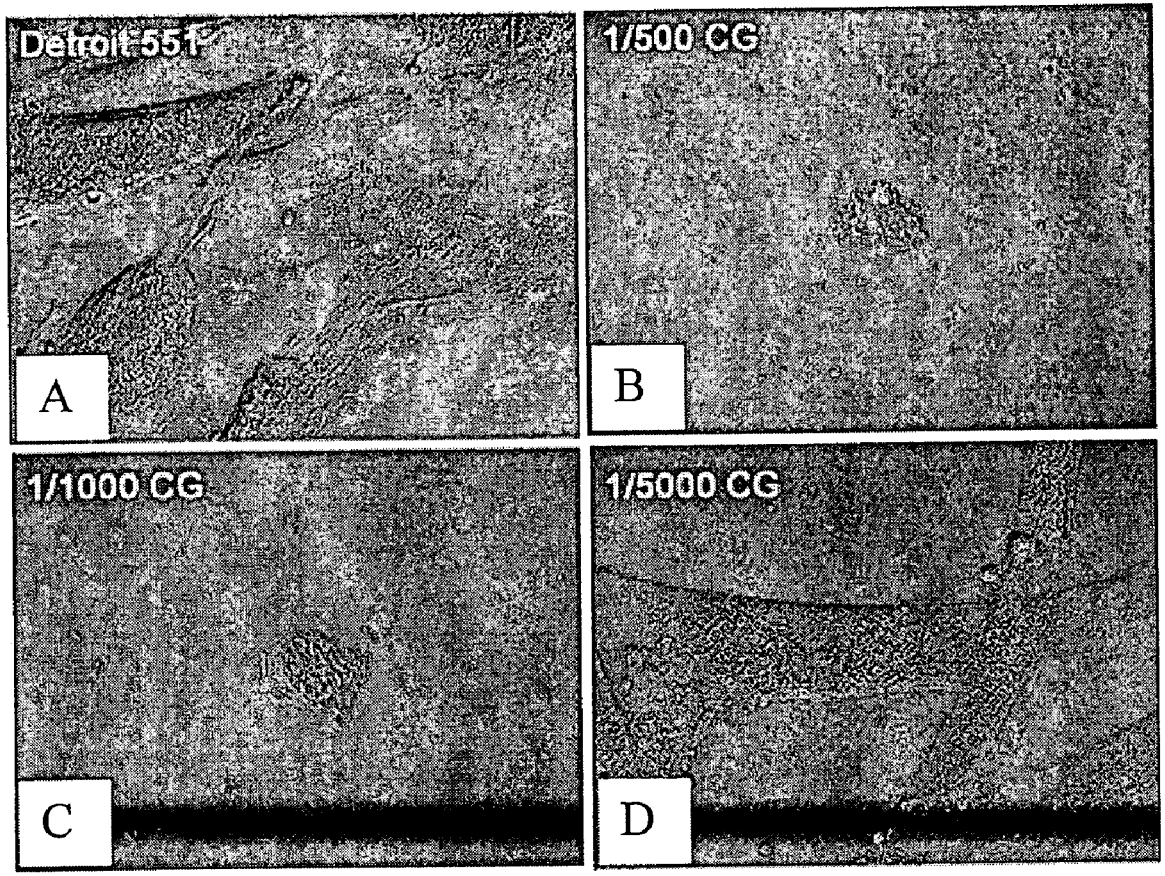
FIG. 3 shows DIC microscope images of Detroit 551 without the treatment of abietic acid (panel A) or treated with 0.3 $\mu g/ml$ (1/500 dilution, panel B), 0.15 $\mu g/ml$ (1/1000 dilution, panel C) and 0.03 $\mu g/ml$ (1/5000 dilution, panel D) abietic acid, respectively.

To the end of the period, all the mice were alive. The maximum diameter of the tumor on the back of each nude mouse of the control group and the experimental group were recorded, as shown in Table 1 and FIG. 3.

TABLE 1

Tumor size of each mouse and the average tumor size thereof

| Weeks | Maximum diameter of the tumor (cm) | | | | | | | | Average maximum diameter |
|---|---|---|---|---|---|---|---|---|---|
| Control Group (without abietic acid treatment) | | | | | | | | | |
| 1 | 0.8 | 0.9 | 0.5 | 0.5 | 0.4 | 0.4 | 0.4 | 0.7 | 0.575 |
| 3 | 1.0 | 1.1 | 0.6 | 0.5 | 0.5 | 0.5 | 0.4 | 0.8 | 0.675 |
| 6 | 1.3 | 1.4 | 0.8 | 0.6 | 0.6 | 0.6 | 0.5 | 0.8 | 0.825 |
| 9 | 1.6 | 1.5 | 1.1 | 0.8 | 0.8 | 0.8 | 0.6 | 0.9 | 1.012 |
| 12 | 1.8 | 1.7 | 1.2 | 1.0 | 1.0 | 0.9 | 0.8 | 1.1 | 1.187 |
| Experimental Group (with abietic acid treatment) | | | | | | | | | |
| 1 | 0.7 | 0.5 | 0.6 | 0.6 | 0.5 | 0.7 | 0.4 | 0.7 | 0.587 |
| 3 | 0.8 | 0.6 | 0.7 | 0.7 | 0.6 | 0.7 | 0.5 | 0.8 | 0.675 |
| 6 | 0.8 | 0.7 | 0.7 | 0.7 | 0.6 | 0.8 | 0.5 | 0.8 | 0.700 |
| 9 | 0.9 | 0.8 | 0.8 | 0.8 | 0.7 | 0.8 | 0.6 | 0.9 | 0.787 |
| 12 | 0.9 | 0.8 | 0.8 | 0.9 | 0.7 | 0.8 | 0.6 | 0.9 | 0.800 |

Figure 4:
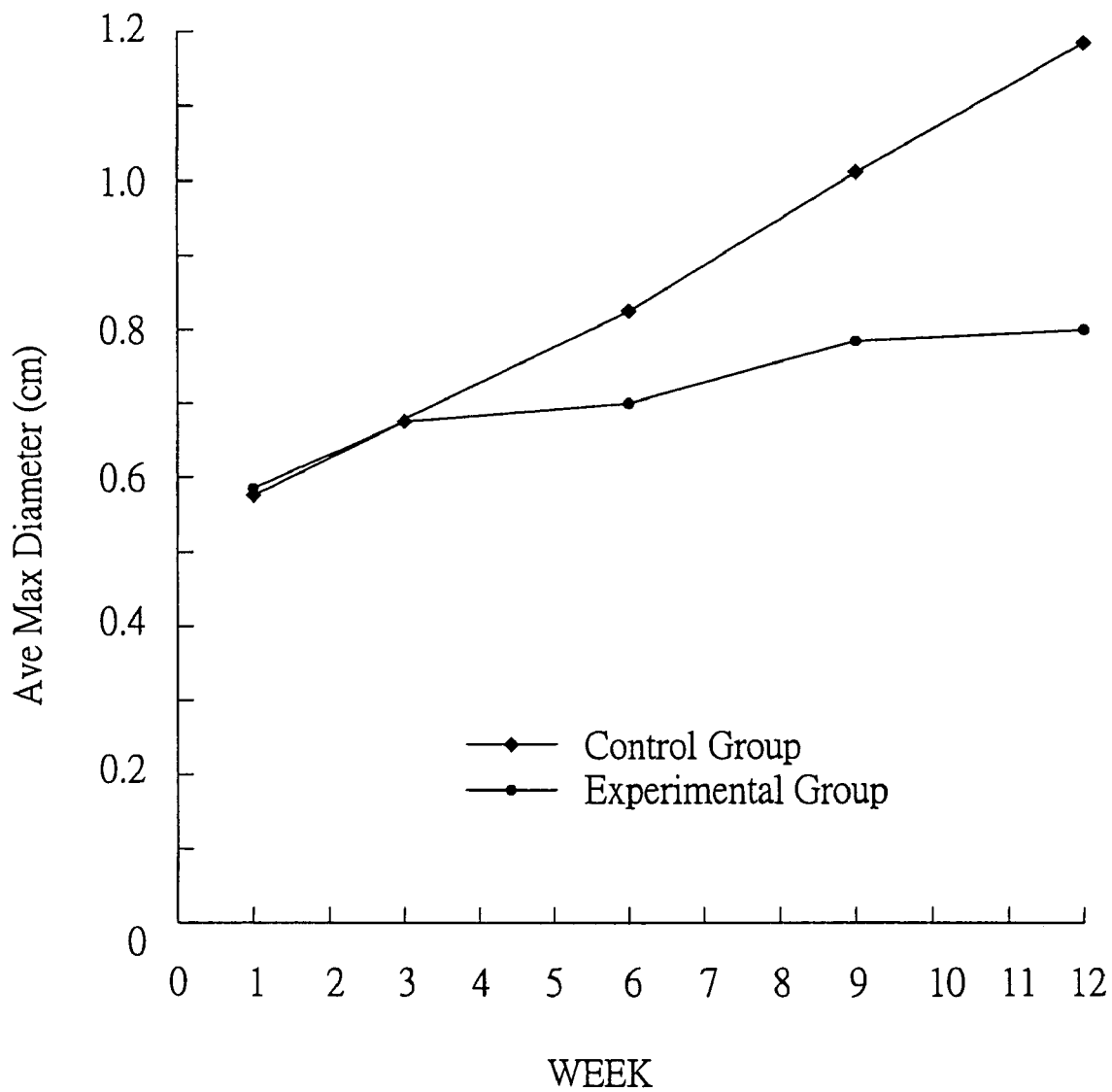
FIG. 4 illustrates an average maximum diameter of the tumor on the mice without the treatment of abietic acid (control group) or treated with abietic acid (experimental group).

As shown in Table 1 and FIG. 4, the average maximum diameter of the tumor on the mice treated with abietic acid is significantly reduced in comparison with that of the mice without the abietic acid treatment. It is concluded that Abietic acid can reduce the tumor size of a cancer, particularly a breast cancer.

Example 3

A MTT (mitochondrial activity) assay was used to determine a cell proliferation. It was found that abietic acid could by itself inhibit cell mitosis in a dose-dependent manner and significantly enhanced the killing effects of a variety of anti-cancer drugs.

In addition, to further study the mechanisms underlying the swelling phenomenon of a cell, electrophysiological experiments and dye-permeability assays were conducted to measure the permeability of a plasma membrane of the cell. It was found that abietic acid would have a direct effect on influx and efflux of chemicals across the cell membrane.

What is claimed is:

1. A method for enhancing the inhibitory activity of an anticancer drug in cervical carcinoma cells, hepatocellular carcinoma cells, or breast cancer cells, comprising administering to the cells abietic acid or dehydroabietic acid in combination with the anticancer drug.

2. The method of claim 1, wherein the cells are human.

3. The method of claim 1, wherein the abietic acid or dehydroabietic acid and anticancer drug are administered simultaneously.

4. The method of claim 1, wherein the abietic acid or dehydroabietic acid and anticancer drug are administered sequentially.

5. The method of claim 1, wherein the anticancer drug is taxol.

6. The method of claim 1, wherein the anticancer drug is mitomycin.

7. A method for increasing the permeability of cervical carcinoma cells, hepatocellular carcinoma cells, or breast cancer cells, comprising contacting the cells with abietic acid or dehydroabietic acid in combination with an anticancer drug.

8. The method of claim 7, wherein the cells are human.

9. The method of claim 7, wherein the cells swell and become round in morphology after exposure to abietic acid or dehydroabietic acid.

* * * * *